United States Patent [19]
Kawase et al.

[11] Patent Number: 6,146,862
[45] Date of Patent: Nov. 14, 2000

[54] THERMOSTABLE DIAPHORASE GENE

[75] Inventors: Shido Kawase; Hitoshi Kondo; Munehiko Dombou, all of Kyoto, Japan

[73] Assignee: Unitaka Ltd., Hyogo, Japan

[21] Appl. No.: 09/075,194

[22] Filed: May 11, 1998

[30] Foreign Application Priority Data

May 9, 1997 [JP] Japan ..................................... 9-119966

[51] Int. Cl.⁷ .............................. C12N 9/02; C12N 1/20; C12N 1/14; C12N 15/00; C07H 21/04
[52] U.S. Cl. ................. 435/189; 435/252.3; 435/252.33; 435/254.11; 435/320.1; 536/23.2
[58] Field of Search ................................ 435/189, 252.3, 435/252.33, 254.11, 320.1; 536/23.2

[56] References Cited

PUBLICATIONS

Rudinger (1976) Characteristics of the amino acids as components of a peptide hormones sequence. In: Peptide Hormone. Ed. J. A. Parsons. University Park Press, Baltimore, MD. pp. 1–7, Jan. 1976.

Ngo et al. (1994) Computational complexity, protein structure prediction, and the ILevinthal paradox. In: The Protein Folding Problem and Tertiary Structure Prediction. Eds. Merz et al. Birkhauser et al. Boston, MA. pp. 491–495, Jan. 1994.

Thornton et al. (1995) Protein Engineering: Editorial Overview. Current Opinion in Biotechnology 6(4): 367–369, Sep. 1995.

Wallace (1993) Understanding cytochrome c function: engineering protein structure by semisynthesis. The FASEB Journal 7: 505–515., Apr. 1993.

Mains et al. (1980) Purification of an NADH–(dichlorophenol–indophenol) oxidoreductase from Bacillus stearothermophilus, Biochemical Journal. 191 (2): 457–465, Nov. 1980.

Matsudira (1991) Limited N–terminal sequence analysis. Methods in Ehzymology.182: 602–613, Feb. 1991.

Wozney (1991) Using purified protein to clone its gene. Methods in Enzymology. 182: 738–751, Feb. 1991.

Maniatis et al. (1982) Chapter 12: Vectors that express cloned DNA in *Escherichia coli*. In Molecular Cloning: A Laboratory Manual. Cold Spring Harbor Laboratory Press. pp. 404–433, Jan. 1982.

Pharmacia Catalog (1997) Catalog No. 27–4935–01. p. 87, Jan. 1997.

*Primary Examiner*—Einar Stole
*Attorney, Agent, or Firm*—Wenderoth Lind & Ponack, L.L.P.

[57] ABSTRACT

The present invention provides a gene derived from a thermophilic Bacillus, comprising the nucleotide sequence of SEQ ID No.2 and encoding a thermostable diaphorase comprising the amino acid sequence of SEQ ID No.1, a recombinant vector possessing the gene, a transformant with the recombinant vector and a process for producing the thermostable diaphorase by using the transformant.

13 Claims, 1 Drawing Sheet is gene, a recombinant vector possessing the gene, a transformant with the recombinant vector, and a process for producing a thermostable diaphorase using the transformant.

THERMOSTABLE DIAPHORASE GENE

BACKGROUND OF THE INVENTION

DESCRIPTION OF THE RELATED ART

1. Field of the Invention

The present invention relates to a thermostable diaphorase gene, a recombinant vector possessing the gene, a transformant with the recombinant vector, and a process for producing a thermostable diaphorase using the transformant.

2. Background of the Invention

Diaphorase [EC.1.6.99.-] is an enzyme functioning a significant role in the electron transport systems in vivo, and is also an industrially useful enzyme in vitro. That is, the diaphorase is an essential component for a clinical specimen in which NDA (nicotineamide adenine dinucleotide) reactions are involved. Diaphorase is currently prepared through isolation and purification from microorganisms. For example, microorganisms belonging to Clostridium (Kaplan, N. O., et al., Arch. Biochem. Biophys., Vol.132, p.91–98, 1969) and Bacillus have been known as microorganisms with diaphorase producing ability, which are commercially available from Sigma, Co. and Asahi Chemical Industry, Co., respectively. However, the yield of diaphorase obtained from these microorganisms is low and the diaphorase obtained is thermally unstable, and hence the purification of the diaphorase requires extremely laborious work.

The present inventors have found that thermophilic *Bacillus stearothermophilus* produces thermostable diaphorase endogenously, and have obtained the patents of the thermostable diaphorase-producing bacterium and a method for purifying the diaphorase (Japanese Patent Nos. 1715795 and 1973434).

According to these patented inventions, diaphorase with excellent thermal stability and stability under storage can be recovered and the purification thereof can be attained. However, since the thermostable diaphorase is produced by culturing the bacteria generally at a high temperature of 50 to 60° C. in accordance with the patented invention described above, a vast amount of energy is required. In addition, the yield of diaphorase obtained from the bacteria is at a low level as same as conventional diaphorase. Thus, the difficulty of mass producing thermostable diaphorase has not yet been solved.

SUMMARY OF THE INVENTION

It is an object of the present application to provide materials for producing thermostable diaphorase at a mass scale in a genetic engineering manner, and a process for producing the thermostable diaphorase using the materials.

The first embodiment of the present invention provided by the present application is a gene derived from a thermophilic Bacillus, encoding a thermostable diaphorase comprising the amino acid sequence of SEQ ID No.1.

The second embodiment of the present invention is a gene derived from a thermophilic Bacillus, encoding a thermostable diaphorase consisting of an amino acid sequence of which one or more amino acid residues are deleted from, substituted for, or added to the amino acid sequence of SEQ ID No.1.

The third embodiment of the present invention is a gene derived from a thermophilic Bacillus, comprising the nucleotide sequence of SEQ ID No.2 and encoding a thermostable diaphorase.

The fourth embodiment of the present invention is a gene derived from a thermophilic Bacillus, consisting of a nucleotide sequence of which one or more nucleotides are deleted from, substituted for, or added to the nucleotide sequence of SEQ ID No.2 and encoding a thermostable diaphorase.

As a preferable embodiment of the above, the thermophilic Bacillus is *Bacillus stearothermophilus*.

The fifth embodiments of the present invention is a recombinant vector, which is a vector DNA possessing a DNA fragment comprising any one of the genes of the 1st–4th embodiments.

In the recombinant vector, the vector DNA is a plasmid DNA of which host cell is *Escherichia coli*, which is for example pKK233-3.

The sixth embodiments of the present invention is a transformant, which is a cell transformed with the recombinant vector of the 5th embodiment.

The seventh embodiment of the present invention is another transformant, which is *Escherichia coli* transformed with the recombinant vector derived from pKK233-3 for example.

The eighth embodiment of the present invention is a process for producing a thermostable diaphorase, comprising culturing the transformant of the 6th or 7th embodiment in a culture medium and isolating the thermostable diaphorase from the cultured transformant.

DETAILED DESCRIPTION OF THE PREFERRED EMBODIMENT

Figure 1:
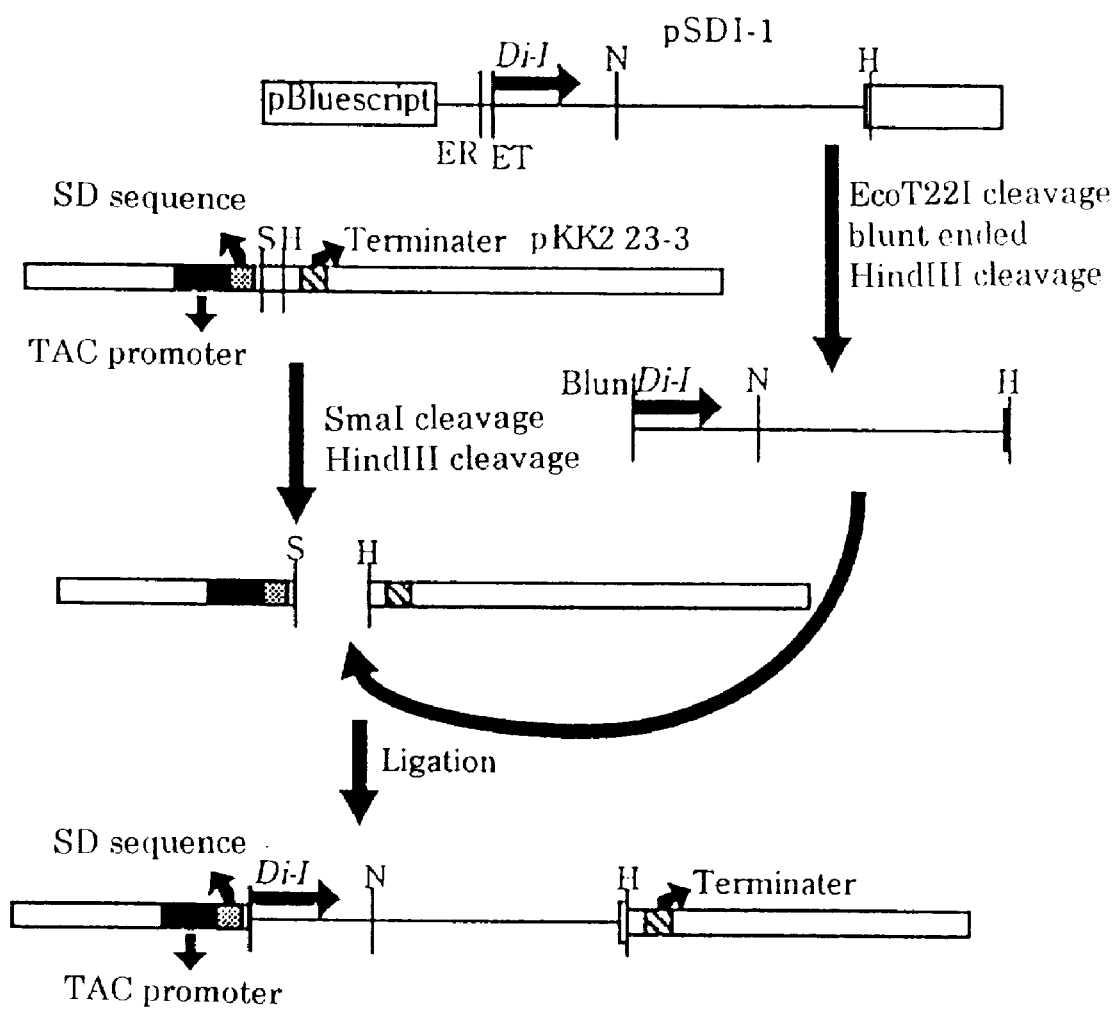
FIG. 1 schematically shows a view of preparing pSDE1 as one example of the recombinant vector in accordance with the present invention. In the figure, "ER" represents EcoR; "ET" represents EcoT22; "N" represents NaeI; "S" represents SmaI; "H" represents HindIII; "Terminator" represents RNA polymerase elimination sequence; "SD" represents ribosome binding sequence; and "TAC promoter" represents RNA polymerase-binding site.

The thermostable diaphorase in accordance with the present invention is a protein with the amino acid sequence of SEQ ID No.1 or a protein with an amino acid sequence of which one or more amino acid residues is deleted from, substituted for, or added to the amino acid sequence of SEQ ID No.1. Accordingly, the gene of the present invention is a gene encoding the amino acid sequence mentioned above, and more specifically, a gene comprising the nucleotide sequence of SEQ ID No.2.

Such gene can be obtained, for example, in a process of synthesizing partially the sequence of SEQ ID NO.2 and cloning the target gene from a DNA library by using the synthesized DNA as a probe, or a process of amplifying the objective gene by PCR method using the synthesized oligontucleotides corresponding to both end of SEQ ID No.2 as primers and the chromosomal DNA as a template.

For the thermophilic Bacillus, for example, UK-563 (FERM P-7275), ACTT-7953 (FERM P-4775), ACTT-8005 (FERM P-4776), ACTT-10149 (FERM P-4777), NCA-1503 (FERM P-4778), SP-43 (FERM P-12754) and the like may be used.

The isolation of the thermostable diaphorase gene from the Bacillus, preparations of a recombinant vector possessing the gene and a transformant with the recombinant vector, and the culturing of the transformant can be carried out by combining together for example the methods described in Molecular Cloning (Sambrook, J., et al., Cold Spring Harbor Laboratory Press, Cold Spring Harbor, 1989). Furthermore, the thermostable diaphorase can be prepared, by subjecting the collected transformant to lysis with ultrasonic wave or lysozyme prior to centrifugation and passing the resulting supernatant through commercially available ion exchange resins or affinity resins or the like, to separate the thermostable diaphorase.

EXAMPLES

The present invention will now be described more specifically and in more detail in the following examples. However, the examples should in no way limit the scope of the claims.

Example 1
Identification of Thermostable Diaphorase Gene
(1) Preparation Chromosomal DNA Library of *Bacillus stearothermophilus*

One gram of the bacteria of thermophilic *Bacillus stearothermophilus* UK-563 (FERM P-7275) was subjected to lysis with lysozyme (manufactured by Biochemical Industry, Co.) according to the known method (Saito & Miura, Biochim. Biophys., Acta, Vol.72, p.619, 1963), to extract the DNA into an alkaline buffer containing SDS and phenol. Furthermore, the RNA was degraded with RNase, to purify the chromosomal DNA (1 mg).

One hundred micrograms of the resulting chromosomal DNA was partially digested with restriction enzyme Sau3Al (manufactured by Toyobo, Co. Ltd.), to obtain a chromosomal DNA fragment (80 μg).

Alternatively, 1 μg of vector pUC19 (manufactured by Takara Suzou, Co.) was completely digested with BamHI (manufactured by Toyobo, Co. Ltd.), and was then treated with an alkali phosphatase derived from a bacterium (manufactured by Takara Suzou, Co. Ltd.), to obtain a vector DNA fragment (0.8 μg). By using T4 ligase-derived DNA ligase (manufactured by Takara Suzou, Co. Ltd.), the resulting chromosomal DNA fragment (0.28 μg) was ligated to the vector DNA fragment (0.1 μg) at 16° C. for 30 minutes, thereby obtaining a recombinant DNA. The resulting recombinant DNA was mixed with 200 μg of *Escherichia coli* JM109 competent cell (manufactured by Toyobo, Co. Ltd.), and the resulting mixture was stored at 0° C. for one hour, followed by heating at 42° C. for 120 seconds, whereby transformation was effected.

The resulting transformant was inoculated into an L medium of 1 ml, for culturing at 37° C. for one hour, and the resulting culture broth was coated on an agar plate medium containing ampicillin, to generate an ampicillin-resistant bacterial strain. The bacterial strain was cultured in an L medium containing 50 μg/ml ampicillin, for overnight culturing, and after harvesting the bacteria, a plasmid was prepared by the alkali-SDS method, which was defined as a chromosomal DNA library of *Bacillus stearothermophilus*.
(2) Isolation of the Thermostable Diaphorase Gene Endonuclease and Exonuclease III (manufactured by GIBCO BRL, Co.) were sequentially reacted with the *Bacillus stearothermophilus* chromosomal DNA library, and a single-stranded DNA library was prepared. Biotinylated diaphorase probes (Di-IF and Di-IR) and magnetic beads with streptoavidin immobilized thereon were mixed with the single-stranded DNA library, and by utilizing the strong specific binding between biotin and streptoavidin, a single-stranded clone which hybridized with the probes was screened by means of a magnet. By using Di-IF and Di-IR as the primers, the screened single-stranded clone was prepared into a double-stranded plasmid, which was then mixed into 200 μg of *Escherichia coli* JM109 competent cell (manufactured by Toyobo, Co., Ltd.) and was then stored at 0° C. for one hour, followed by heating at 42° C. for 120 seconds, whereby transformation was effected. The resulting transformant was inoculated into an L medium of 1 ml, for culturing at 37° C. for one hour, and the resulting culture broth was coated on an agar plate medium containing 50 μg/ml ampicillin, to obtained 10 colonies of ampicillin-resistant bacterial strains.

So as to screen a bacterial strain carrying the thermostable diaphorase gene from the colonies, colony-PCR was performed by using Di-IF and Di-IR as the primers and DNA polymerase derived from *Thermus aquaticus* (manufactured by Toyobo, Co. Ltd.), according to the known method (Simpson et al., Biochem. Biophys. Res. Commun., Vol.151, p.487, 1988), and it was indicated that four bacterial strains contained the diaphorase gene.
(3) Determination of the Nucleotide Sequence of the Thermostable Diaphorase Gene One strain was selected from the four transformant strains, and was then inoculated in an L medium (100 ml) containing ampicillin 50 μg/ml. After culturing the strain at 37° C., the plasmid was prepared by the alkali-SDS method, which was defined as plasmid pSD1. After denaturing pSD1 (10 μg) with an alkali, chain termination reaction was conducted by using an M13 universal primer and an M13 reverse primer, according to the known method (Sanger, Nicklen & Coulson, Proc. Natl. Acad. Sci., Vol. 74, p.5463, 1977). For the reaction, Auto Read Sequence Kit (manufactured by Pharmacia, Co.) was used. The reaction product was analyzed by using ALF DNA Sequencer (manufactured by Pharmacia, Co.), to determine the nucleotide sequence of 633 base pairs as shown in SEQ ID No.2.

Example 2
Preparation of Recombinant Vector and Transformed *Escherichia coli*

The plasmid pSD1 was cleaved at the site of EcoT221 (product of Toyobo, Co. Ltd.) which is positioned at the first nucleotide upstream of the diaphorase gene, to prepare the plasmid into a linear form, which was then blunt ended with T4 phage-derived DNA polymerase (manufactured by Takara Suzou, Co. Ltd.) and was further cleaved with HindIII (product of Toyobo Co. Ltd.). Individual fragments of the cleaved linear plasmid was subjected to agarose gel electrophoresis, to obtain a DNA fragment comprising the diaphorase gene. Alternatively, pKK223-3 (manufactured by Pharmacia, Co.) was cleaved at the site of SmaI (product of Toyobo, Co. Ltd.) which is positioned at the 12th nucleotide downstream of the SD sequence and at the multi-cloning site with HindIII (product of Toyobo, Co. Ltd.).

By using T4 phage-derived DNA ligase (product of Takara Suzou, Co. Ltd.), the DNA fragment (0.1 μg) comprising the diaphorase gene and the vector DNA fragment (0.1 μg) were ligated together at 16° C. for 30 minutes, to obtain a recombinant plasmid vector pSDE1 possessing the thermostable diaphorase gene. FIG. 1 schematically shows the scheme of the preparation procedures of the recombinant vector pSDE1.

Then, pSDE1 was mixed with 200 μg of JM109 competent cell (200 μg; manufactured by Toyobo, Co., Ltd.) and was then stored at 0° C. for one hour, followed by heating at 42° C. for 120 seconds, to transform the cell with the pSDE1. The resulting transformant was inoculated in an L medium (1 ml) for culturing at 37° C. for one hour, and the resulting culture broth was coated on an agar plate medium containing 50 μg/ml ampicillin, to generate a colony of 100 bacteria of a transformed *Escherichia coli* containing the thermostable diaphorase gene. One of the bacteria has been deposited as *Escherichia coli* JM109/pSDE1 on Mar. 21, 1997 at National Institute of Bioscience and Human-Technology, the Agency of Industrial Science and Technology, MITI (Deposit Number; FERM BP-6325).

Example 3

Production of Thermostable Diaphorase by *Escherichia coli*

The transformed *Escherichia coli* JM109/pSDEI prepared in Example 3 was inoculated in an L medium (300 ml) containing 50 μg/ml ampicillin, for overnight pre-culturing at 37° C. The pre-culture broth was inoculated in an L medium (30 liters) containing 50 μg/ml ampicillin for culturing at 37° C. for 10 hours, followed by addition of 1 mM isopropyl β-thiogalactopyranoside, for further culturing for another 15 hours. Then, the bacteria were harvested. The resulting bacteria were suspended in 25 mM phosphate buffer, pH8.0 (1000 ml), for ultrasonication. The disrupted bacteria were discarded, and thermostable diaphorase was purified from the resulting supernatant by ion exchange chromatography by means of DEAE Sepharose and affinity chromatography by means of Blue-Sepharose. Thermostable diaphorase was recovered at a yield of 180,000 units, which is 10-fold the yield of the diaphorase recovered by culturing 30 liters of *Bacillus stearothermophilus* UK-563 (FERM P-7275).

The properties of the recovered diaphorase were examined. The residual activity of the diaphorase after treatment at 50° C. for one hour was 100%; the optimum pH was pH 8.0; and Km for NADH was 0.5 mM. Based on these results, it was verified that the thermostable diaphorase obtained by the present invention had the same properties as those of the diaphorase derived from *Bacillus stearothermophilus* UK-563 (FERM P-7275).

The activity of diaphorase was assayed as follows; and the activity is expressed as described hereinbelow. More specifically, the activity was assayed, by mixing an enzyme solution with 1.0 ml of a solution containing 50 mM Tris-HCl buffer, pH 8.5, 1 mM reduction type nicotineamide adenine dinucleotide (NADH) and 0.06 mM 2,6-dichlorophenol indophenol (DCIP), and determining the initial rate of the change of the absorbance at 600 nm at 30° C. One unit of the enzyme activity is the amount of the enzyme required for the reduction of 1 μmol DCIP under the aforementioned conditions for one minute.

As has been described in detail, the thermostable diaphorase can be produced at a large scale in a simple manner at low cost.

What is claimed is:

1. An isolated polynucleotide encoding a thermostable diaphorase comprising the amino acid sequence of Seq ID No:1.

2. The isolated polynucleotide according to claim 1, which comprises the nucleotide sequence of Seq ID No:2.

3. The isolated polynucleotide according to claim 1, which is derived from a thermophilic Bacillus.

4. The isolated polynucleotide according to claim 3, wherein the thermophilic Bacillus is *Bacillus stearothermophilus*.

5. A recombinant vector comprising the isolated polynucleotide of claim 1 or 2.

6. The recombinant vector according to claim 5, which is a plasmid.

7. The recombinant vector according to claim 6, wherein the plasmid transforms the host cell of *Escherichia coli*.

8. The recombinant vector according to claim 6, wherein the plasmid is pKK233-3.

9. A transformant comprising the isolated polynucleotide of claim 1 or 2.

10. A transformant transformed with the recombinant vector of claim 5.

11. A transformed *Escherichia coli* comprising the recombinant vector of claim 7.

12. A method of producing a thermostable diaphorase comprising culturing the transformant of claim 10 in a culture medium, and isolating the thermostable diaphorase from the cultured transformant.

13. A thermostable diaphorase comprising the amino acid sequence of SEQ ID No. 1.

* * * * *

UNITED STATES PATENT AND TRADEMARK OFFICE
CERTIFICATE OF CORRECTION

PATENT NO.     : 6,146,862
DATED          : November 14, 2000
INVENTOR(S)    : Shido Kawase et al.

It is certified that error appears in the above-identified patent and that said Letters Patent is hereby corrected as shown below:

<u>Title page,</u>
Item [73] Assignee: change "Unitaka Ltd." to -- Unitika Ltd. --.

Signed and Sealed this

Twenty-third Day of October, 2001

Attest:

NICHOLAS P. GODICI
Attesting Officer    Acting Director of the United States Patent and Trademark Office

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 211 amino acid residues
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
                20                  25                  30

Val His Pro Asp His Glu Val Ile His Leu Asp Leu Tyr Lys Glu Tyr
                35                  40                  45

Ile Pro Glu Ile Asp Val Asp Val Phe Ser Gly Trp Gly Lys Leu Arg
        50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
                100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Lys Lys Ala Leu His Ile
        130                 135                 140

Gln Ala Arg Gly Gly Phe Tyr Ser Glu Gly Pro Ala Ala Glu Met Glu
145                 150                 155                 160
```

```
Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

(2) INFORMATION FOR SEQ ID NO:2:

(i) SEQUENCE CHARACTERISTICS:
        (A) LENGTH: 633 bases
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Bacillus stearothermophilus
        (B) STRAIN: UK-563 (FERM P-7275)

(xi) SEQUENCE DESCRIPTION: SEQ ID NO:2:

ATGACAAACG TATTGTACAT CACCGCCCAT CCGCACGACG ACACGCAGTC TTACAGCATG      60

GCGGTCGGAA AAGCGTTTAT CGACACATAC AAACAAGTGC ATCCGGATCA TGAAGTCATT     120

CATCTTGACT TATACAAGGA ATACATTCCG GAAATCGACG TCGACGTGTT CAGCGGCTGG     180

GGCAAACTTC GCTCCGGGAA ATCGTTTGAA GAGCTGTCTG ACGAAGAAAA AGCGAAAGTC     240

GGGCGGATGA ACGAGCTGTG CGAGCAGTTT ATTTCCGCCG ACAAATATGT ATTCGTCACG     300

CCGATGTGGA ACTTTTCGTT CCCGCCGGTG TTAAAGGCGT ATATTGACGC CGTGGCGGTC     360

GCCGGCAAGA CGTTTAAATA TACGGAACAA GGGCCGGTCG GATTGCTTAC TGATAAAAAA     420

GCGCTCCACA TTCAAGCGCG CGGCGGTTTC TACTCCGAAG GCCCGGCGGC GGAAATGGAA     480

ATGGGCCATC GGTATTTAAG CGTCATCATG CAATTTTTCG GTGTTCCGTC ATTTGAAGGG     540

TTGTTTGTCG AAGGGCATGC GGCGGTGCCG GAAAAGGCGG AAGAAATTAA AGCGAACGCC     600

ATCGCTCGGG CGAAAGACTT GGCGCACACG TTT                                  633
```